United States Patent
Choi et al.

(10) Patent No.: US 10,000,462 B2
(45) Date of Patent: Jun. 19, 2018

(54) OPTOELECTRONIC MATERIAL AND ORGANIC OPTOELECTRONIC DEVICE AND IMAGE SENSOR

(71) Applicant: Samsung Electronics Co., Ltd., Suwon-Si, Gyeonggi-Do (KR)

(72) Inventors: Yeong Suk Choi, Suwon-si (KR); Kwang Hee Lee, Yongin-si (KR); Seon-Jeong Lim, Yongin-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 571 days.

(21) Appl. No.: 14/618,597

(22) Filed: Feb. 10, 2015

(65) Prior Publication Data
US 2015/0325797 A1   Nov. 12, 2015

(30) Foreign Application Priority Data

May 9, 2014 (KR) .......................... 10-2014-0055668

(51) Int. Cl.

| | |
|---|---|
| *C07D 333/50* | (2006.01) |
| *C07D 333/24* | (2006.01) |
| *H01L 51/00* | (2006.01) |
| *H01L 27/30* | (2006.01) |
| *C07D 333/18* | (2006.01) |
| *C07D 409/14* | (2006.01) |
| *C07D 495/04* | (2006.01) |
| *H01L 51/42* | (2006.01) |

(52) U.S. Cl.
CPC ......... *C07D 333/24* (2013.01); *C07D 333/18* (2013.01); *C07D 409/14* (2013.01); *C07D 495/04* (2013.01); *H01L 27/307* (2013.01); *H01L 51/008* (2013.01); *H01L 51/0036* (2013.01); *H01L 51/0043* (2013.01); *H01L 51/0068* (2013.01); *H01L 51/42* (2013.01)

(58) Field of Classification Search
USPC ................................ 549/41, 43–45; 252/500
See application file for complete search history.

(56) References Cited

U.S. PATENT DOCUMENTS

| | | | |
|---|---|---|---|
| 6,403,809 B1 * | 6/2002 | Holmes | ................ C07D 495/04 359/321 |
| 8,999,526 B2 * | 4/2015 | Lee | .................... H01L 51/0068 257/40 |
| 2013/0112947 A1 | 5/2013 | Lee et al. | |

FOREIGN PATENT DOCUMENTS

| | | |
|---|---|---|
| KR | 20110088852 A | 8/2011 |
| KR | 20130050082 A | 5/2013 |

OTHER PUBLICATIONS

Leem, Dong-Seok, et al. "Low dark current small molecule organic photodetectors with selective response to green light"; Applied Physics Letters (2013), vol. 103, issue 043305.

* cited by examiner

*Primary Examiner* — Monique Peets
(74) *Attorney, Agent, or Firm* — Harness, Dickey & Pierce, P.L.C.

(57) ABSTRACT

An optoelectronic material includes a first organic molecule and a second organic molecule crosslinked with each other, the first organic molecule and the second organic molecule having wavelength selectivity in a visible ray region.

18 Claims, 14 Drawing Sheets

OPTOELECTRONIC MATERIAL AND ORGANIC OPTOELECTRONIC DEVICE AND IMAGE SENSOR

PRIORITY STATEMENT

This application claims priority to and the benefit of Korean Patent Application No. 10-2014-0055668 filed in the Korean Intellectual Property Office on May 9, 2014, the entire contents of which are incorporated herein by reference.

BACKGROUND

1. Field

Example embodiments provide an optoelectronic material, an organic optoelectronic device, and an image sensor including the same.

2. Description of the Related Art

An optoelectronic device converts light into an electrical signal, and may include a photodiode and/or a phototransistor. The optoelectronic device may be applied to an image sensor, a solar cell and/or an organic light emitting diode.

An image sensor including a photodiode requires relatively high resolution and thus a relatively small pixel. At present, a silicon photodiode is widely used, but the silicon photodiode has a problem of deteriorated sensitivity because of a relatively small absorption area due to relatively small pixels. Accordingly, an organic material that is capable of replacing silicon has been researched.

The organic material has a relatively high extinction coefficient and selectively absorbs light in a particular wavelength region depending on a molecular structure, and thus may simultaneously replace a photodiode and a color filter and resultantly improve sensitivity and contribute to relatively high integration.

SUMMARY

Example embodiments provide an optoelectronic material being capable of simultaneously improving light absorption characteristics and wavelength selectivity.

Example embodiments also provide organic optoelectronic device including the optoelectronic material.

Example embodiments also provide an image sensor including the organic optoelectronic device.

According to example embodiments, an optoelectronic material includes a first organic molecule and a second organic molecule crosslinked with each other, the first organic molecule and the second organic molecule having wavelength selectivity in a visible ray region.

Each of the first organic molecule and the second organic molecule may independently be one of a thiophene and a thiophene derivative.

The first organic molecule and the second organic molecule may be independently represented by the following Chemical Formula 1.

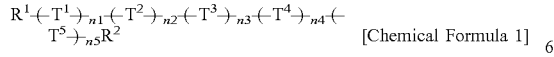

[Chemical Formula 1]

In the above Chemical Formula 1,

Each of $T^1$, $T^2$, $T^3$, $T^4$, and $T^5$ are independently a substituted or unsubstituted thiophene moiety, Each of $R^1$ and $R^2$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a substituted or unsubstituted $C_2$ to $C_{30}$ alkenyl group, a cyano group, a cyanovinyl group, and a combination thereof, Each of n1 to n5 are independently 0 or 1, and at least one of n1 to n5 is 1.

The optoelectronic material may be represented by one of the following Chemical Formulae 1a to 1m.

[Chemical Formula 1a]

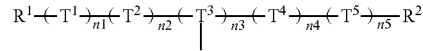

[Chemical Formula 1b]

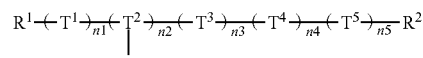

[Chemical Formula 1c]

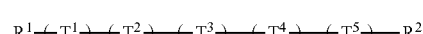

[Chemical Formula 1d]

[Chemical Formula 1e]

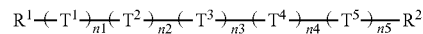

[Chemical Formula 1f]

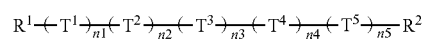

[Chemical Formula 1g]

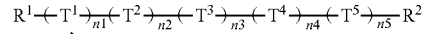

[Chemical Formula 1h]

[Chemical Formula 1i]

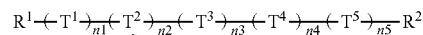

[Chemical Formula 1j]

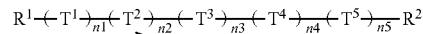

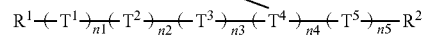

-continued

[Chemical Formula 1k]
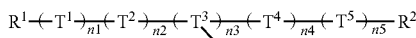
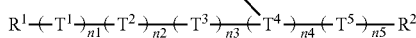

[Chemical Formula 1l]
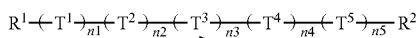
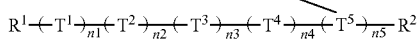

[Chemical Formula 1m]
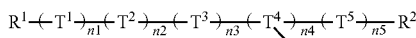
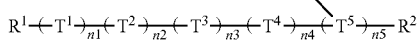

In the above Chemical Formulae 1a to 1m, each of $T^1$, $T^2$, $T^3$, $T^4$, and $T^5$ are independently a substituted or unsubstituted thiophene moiety, each of $R^1$ and $R^2$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a substituted or unsubstituted $C_2$ to $C_{30}$ alkenyl group, a cyano group, a cyanovinyl group, and a combination thereof, Each of n1 to n5 are independently 0 or 1, and At least one of n1 to n5 is 1.

The $T^1$, $T^2$, $T^3$, $T^4$, and $T^5$ may be independently selected from groups listed in the following Group 1.

[Group 1]
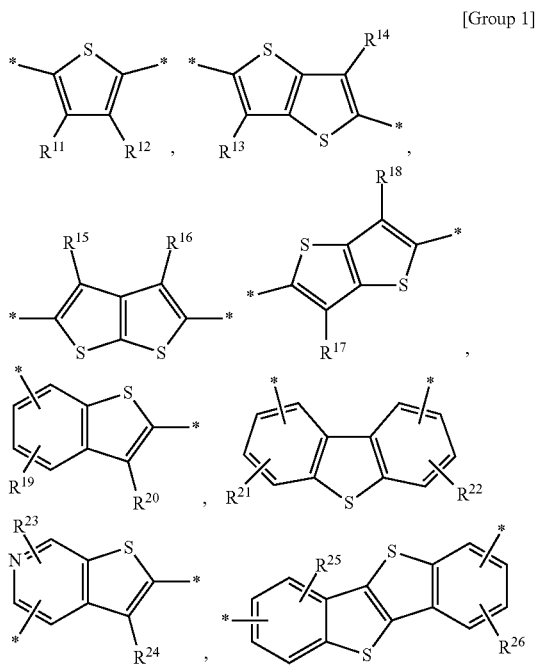

In the Group 1, each of $R^{11}$ to $R^{26}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, and a combination thereof, or a point linked with the first organic molecule or the second organic molecule.

The one of $R^{11}$ to $R^{26}$ of $T^1$, $T^2$, $T^3$, $T^4$, and $T^5$ of the first organic molecule may be linked with one of $R^{11}$ to $R^{26}$ of $T^1$, $T^2$, $T^3$, $T^4$, and $T^5$ of the second organic molecule.

The first organic molecule and the second organic molecule may be independently represented by the following Chemical Formula 2.

[Chemical Formula 2]
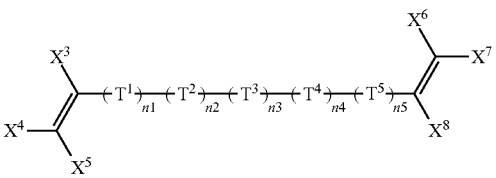

In the above Chemical Formula 2,

Each of $T^1$, $T^2$, $T^3$, $T^4$, and $T^5$ are independently a substituted or unsubstituted thiophene moiety, Each of $X^3$ to $X^8$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a cyano group, and a combination thereof, At least one of $X^3$ to $X^8$ is a cyano group, Each of n1 to n5 are independently 0 or 1, and At least one of n1 to n5 is 1.

The first organic molecule and the second organic molecule may be independently represented by one of the following Chemical Formulae 2a to 2c.

[Chemical Formula 2a]
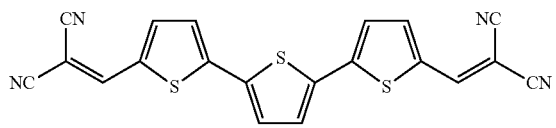

[Chemical Formula 2b]
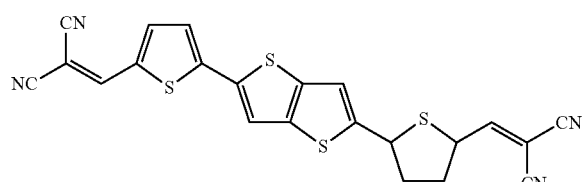

[Chemical Formula 2c]
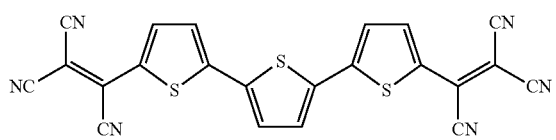

The optoelectronic material may be represented by one of the following Chemical Formulae 2aa to 2cb.

[Chemical Formula 2aa]
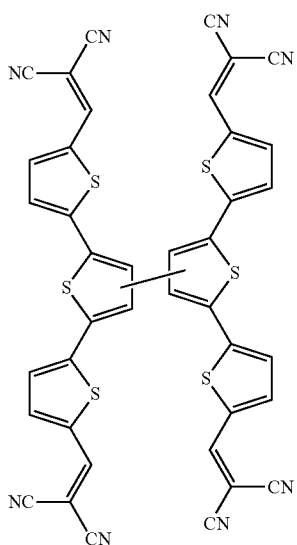
[Chemical Formula 2ba]
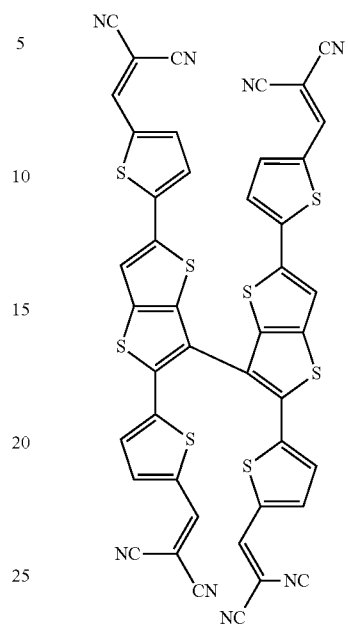
[Chemical Formula 2ab]
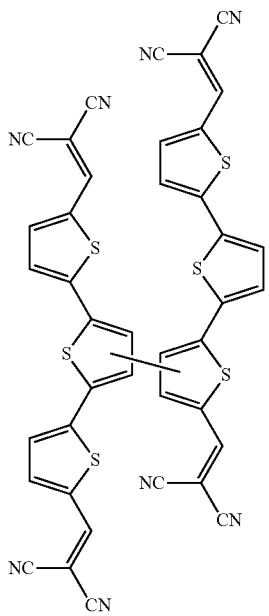
[Chemical Formula 2bb]
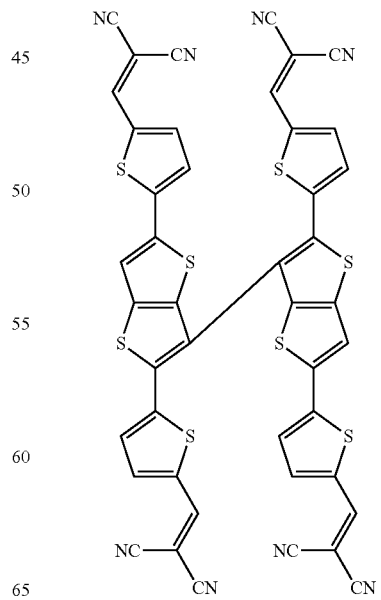

-continued

[Chemical Formula 2bc]

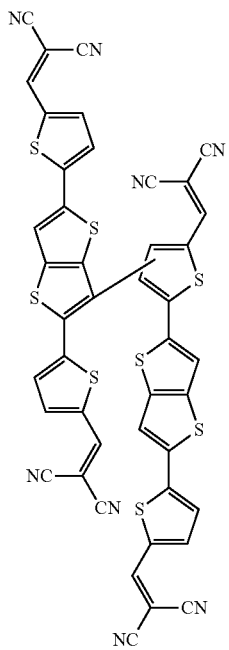

[Chemical Formula 2bd]

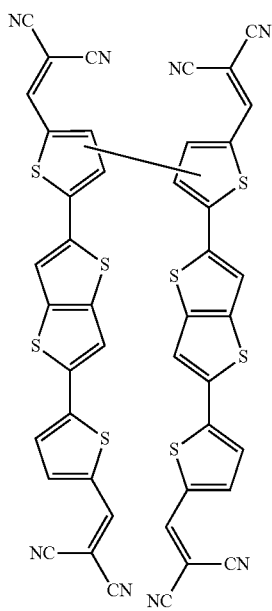

-continued

[Chemical Formula 2ca]

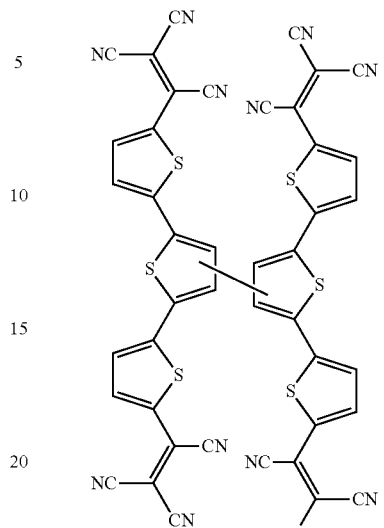

[Chemical Formula 2cb]

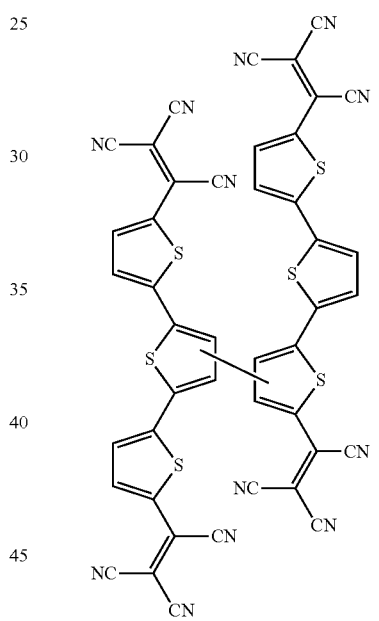

The first organic molecule and the second organic molecule may absorb light in one of a blue wavelength region, a red wavelength region, and a green wavelength region.

The blue wavelength region may have a maximum absorption wavelength ($\lambda_{max}$) at greater than or equal to about 400 nm and less than about 500 nm, the red wavelength region may have a maximum absorption wavelength ($\lambda_{max}$) at greater than about 580 nm and less than or equal to about 700 nm, and the green wavelength region may have a maximum absorption wavelength ($\lambda_{max}$) at about 500 nm to about 580 nm.

The first organic molecule and the second organic molecule may be the same compound.

The optoelectronic material may have a bandgap of about 1.9 to about 2.8 eV.

According to example embodiments, an organic optoelectronic device includes an anode and a cathode facing each other, and an active layer between the anode and the cathode, the active layer including the optoelectronic material.

The organic optoelectronic device may selectively absorb light in a green wavelength region.

The active layer may further include a compound represented by the following Chemical Formula 3.

[Chemical Formula 3]

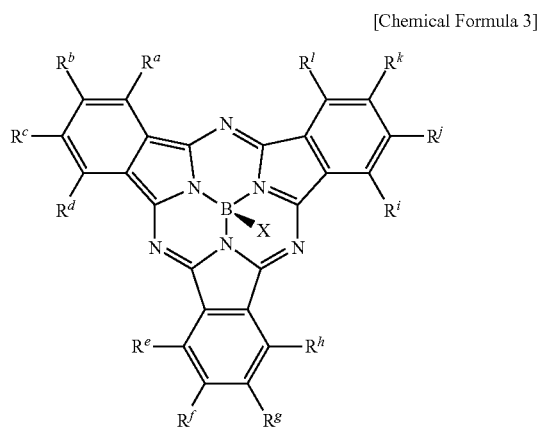

In the above Chemical Formula 3,

Each of $R^a$ to $R^l$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a halogen-containing group, and a combination thereof, and X is an anion.

The compound represented by the above Chemical Formula 3 may further include at least one of compounds represented by the following Chemical Formulae 3a to 3e.

[Chemical Formula 3a]

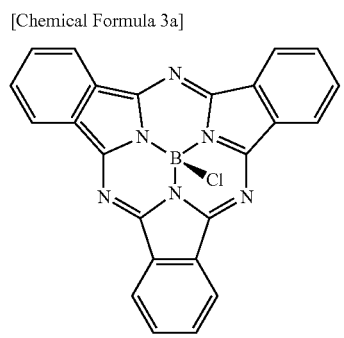

[Chemical Formula 3b]

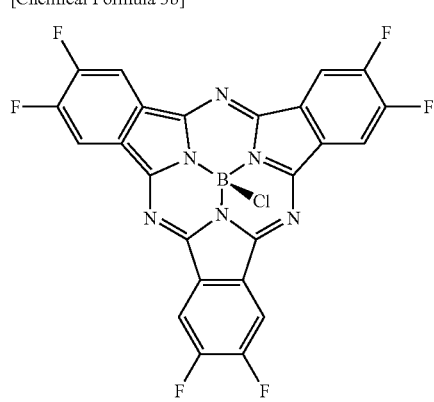

[Chemical Formula 3c]

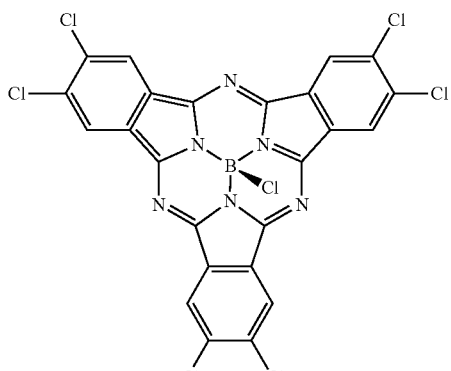

[Chemical Formula 3d]

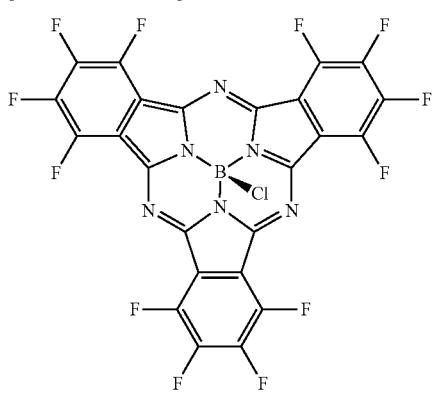

[Chemical Formula 3e]

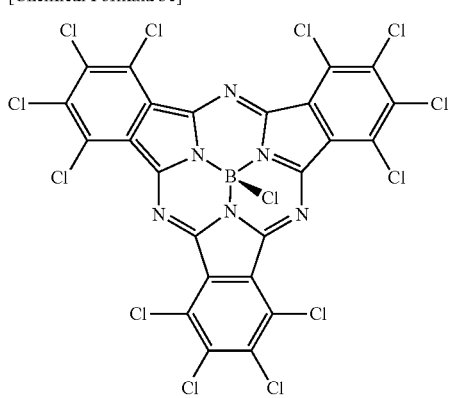

According to example embodiments, an image sensor includes the organic optoelectronic device.

The image sensor may include a semiconductor substrate integrated with a plurality of a first photo-sensing devices sensing light in a blue wavelength region and a plurality of a second photo-sensing device sensing light in a red wavelength region, a color filter layer on the semiconductor substrate and including a blue filter that selectively absorbs light in a blue wavelength region and a red filter that selectively absorbs light in a red wavelength region, and the organic optoelectronic device on the color filter layer.

The organic optoelectronic device may selectively absorb light in a green wavelength region.

DETAILED DESCRIPTION

Figure 1:
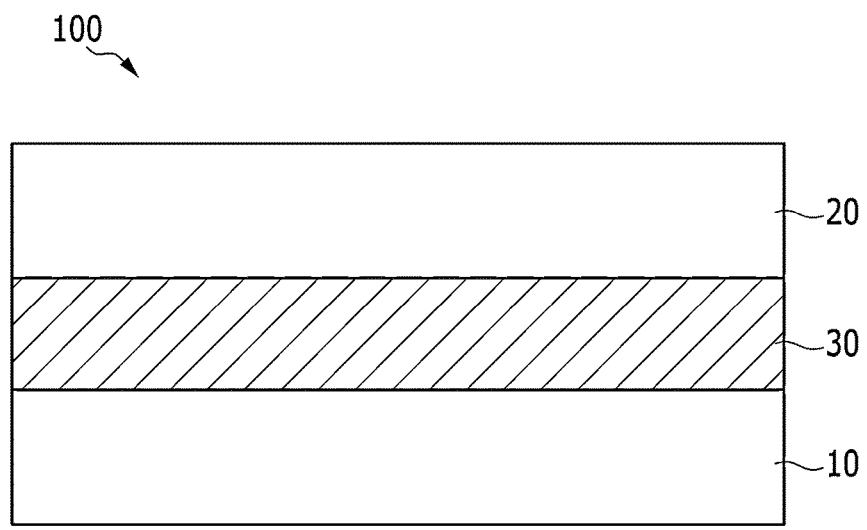
FIG. 1 is a cross-sectional view showing an organic optoelectronic device according to example embodiments.

Example embodiments will hereinafter be described in detail, and may be more easily performed by those who have common knowledge in the related art. However, this disclosure may be embodied in many different forms and is not construed as limited to the example embodiments set forth herein.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms used in the specification (including technical and scientific terms) may be used with meanings commonly understood by a person having ordinary knowledge in the art. Further, unless explicitly defined otherwise, the terms defined in a generally-used dictionary are not ideally or excessively interpreted. In addition, unless explicitly described to the contrary, the word "include" and variations such as "includes" or "including" will be understood to imply the inclusion of stated elements but not the exclusion of any other elements throughout the specification.

As used herein, when a definition is not otherwise provided, the term "substituted" refers to one substituted with a substituent selected from a halogen (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_4$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen of a compound.

As used herein, when specific definition is not otherwise provided, the term "hetero" refers to one including 1 to 3 heteroatoms selected from N, O, S, and P.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

Hereinafter, an optoelectronic material according to example embodiments is described.

The optoelectronic material according to example embodiments is a compound including a first organic molecule and a second organic molecule having wavelength selectivity in a visible ray region and that are crosslinked with each other.

The first and second organic molecules may be the same as or different from each other, and are respectively a light-absorber having a form of a monomer, an oligomer, or a polymer.

The first and second organic molecules are crosslinked and so may increase the total molecular weight of the optoelectronic material and thus the amount of the optoelectronic material in an optical path through which light passes, and resultantly enhance light absorption.

In addition, the first and second organic molecules are crosslinked and thus may decrease thermal motion of the optoelectronic material and cause steric hindrance. Accordingly, the first and second organic molecules may prevent or inhibit crystallization and phase-separation due to excessive thermal motion of the optoelectronic material and increase wavelength selectivity by suppressing π-π interaction in a surface direction, thus preventing or inhibiting a wavelength region for light absorption from being widened.

The first second organic molecules may absorb light in the same wavelength region within a visible ray region; for example, each may absorb light in a blue wavelength region, in a red wavelength region, or in a green wavelength region. The blue wavelength region may have a maximum absorption wavelength ($\lambda_{max}$) at greater than or equal to about 400 nm and less than about 500 nm, the red wavelength region may have a maximum absorption wavelength ($\lambda_{max}$) at greater than about 580 nm and less than or equal to about 700 nm, and the green wavelength region may have a maximum absorption wavelength ($\lambda_{max}$) at about 500 nm to about 580 nm.

The first organic molecule and the second organic molecule may be, for example, the same compound, but are not limited thereto.

The first organic molecule and the second organic molecule may be, for example, thiophene or a thiophene derivative, and may be, for example, represented by the following Chemical Formula 1.

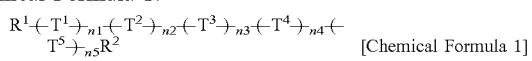  [Chemical Formula 1]

In the above Chemical Formula 1,

Each of $T^1$, $T^2$, $T^3$, $T^4$, and $T^5$ are independently a substituted or unsubstituted thiophene moiety, Each of $R^1$ and $R^2$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a substituted or unsubstituted $C_2$ to $C_{30}$ alkenyl group, a cyano group, a cyanovinyl group, and a combination thereof, Each of n1 to n5 are independently 0 or 1, and At least one of n1 to n5 is 1.

The $T^1$, $T^2$, $T^3$, $T^4$, and $T^5$ may independently be, for example, one selected from groups listed in the following Group 1, but are not limited thereto.

[Group 1]

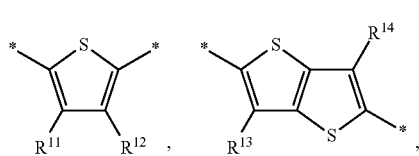

-continued

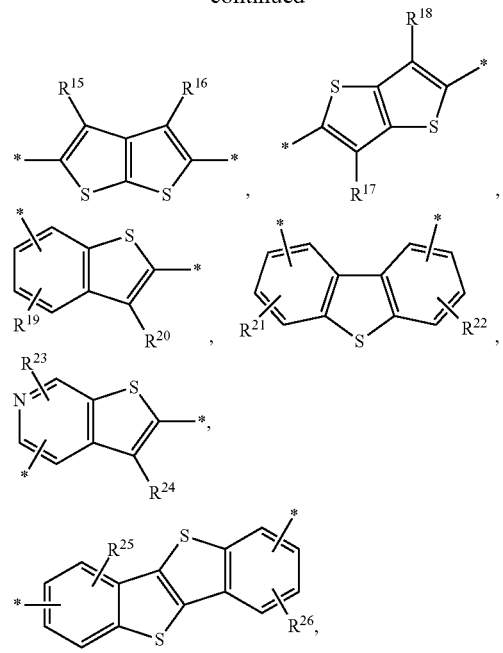

In Group 1,

Each of $R^{11}$ to $R^{26}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, and a combination thereof, or a point linked with the first organic molecule or the second organic molecule.

The first organic molecule and the second organic molecule may be, for example, a thiophene derivative having at least one cyano group, and may be, for example, represented by the following Chemical Formula 2.

[Chemical Formula 2]

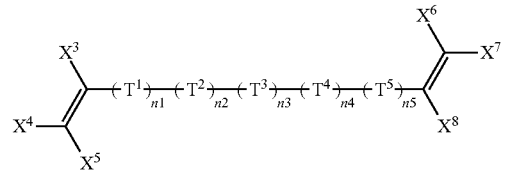

In the above Chemical Formula 2,

Each of $T^1$, $T^2$, $T^3$, $T^4$, and $T^5$ are independently a substituted or unsubstituted thiophene moiety, Each of $X^3$ to $X^8$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a cyano group, and a combination thereof, At least one of $X^3$ to $X^8$ is a cyano group, Each of n1 to n5 are independently 0 or 1, and At least one of n1 to n5 is 1.

For example, the first organic molecule and the second organic molecule may be independently represented by one of the following Chemical Formulae 2a to 2c, but are not limited thereto.

[Chemical Formula 2a]

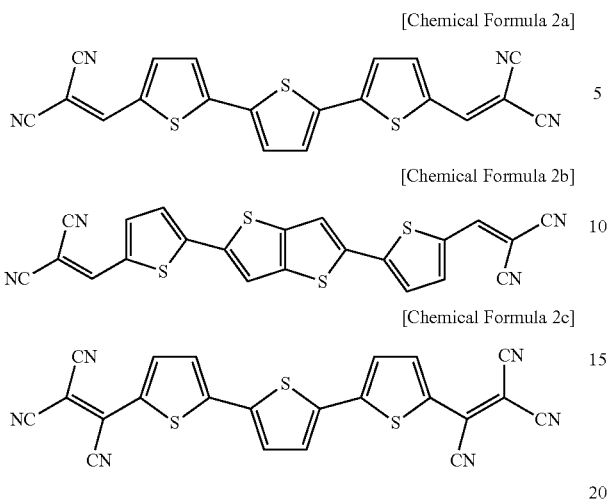

[Chemical Formula 2b]

[Chemical Formula 2c]

The optoelectronic material includes the first and second organic molecules crosslinked with each other, and herein, the first and second organic molecules may have a linking point without a particular limit.

For example, when the first and second organic molecules are individually thiophene or a thiophene derivative, the first and second organic molecules may have a linking point of a thiophene moiety but no thiophene moiety.

For example, in the above Chemical Formula 1 and Group 1, one of $R^{11}$ to $R^{26}$ of $T^1$, $T^2$, and $T^3$ of the first organic molecule may be a linking point with one of $R^{11}$ to $R^{26}$ of $T^1$, $T^2$, and $T^3$ of the second organic molecule.

The optoelectronic material may be, for example, represented by one of the following Chemical Formulae 1a to 1m.

[Chemical Formula 1a]

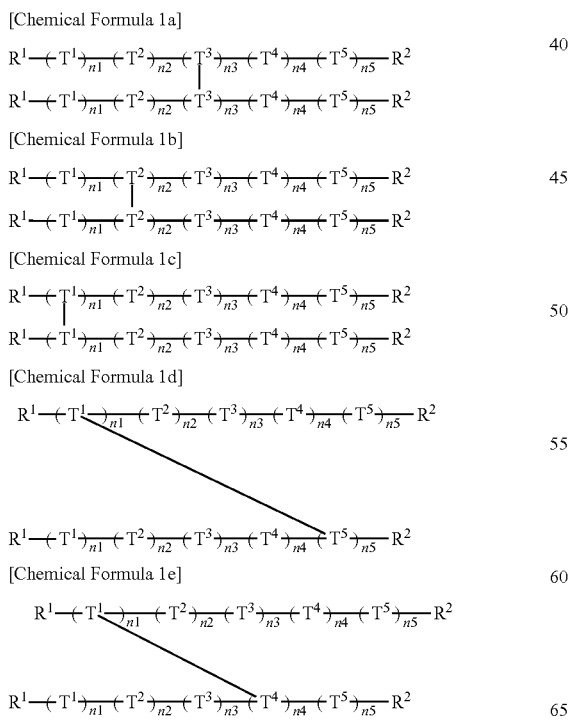

[Chemical Formula 1b]

[Chemical Formula 1c]

[Chemical Formula 1d]

[Chemical Formula 1e]

[Chemical Formula 1f]

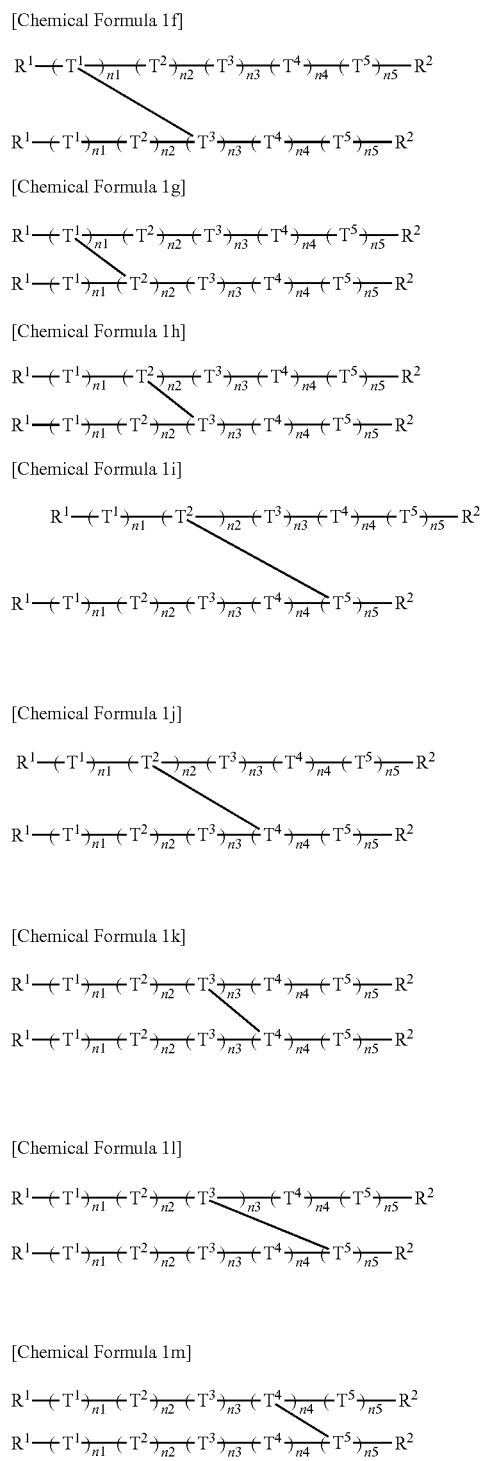

[Chemical Formula 1g]

[Chemical Formula 1h]

[Chemical Formula 1i]

[Chemical Formula 1j]

[Chemical Formula 1k]

[Chemical Formula 1l]

[Chemical Formula 1m]

In the above Chemical Formulae 1a to 1m, $T^1$, $T^2$, $T^3$, $T^4$, $T^5$, $R^1$, $R^2$, and n1 to n5 are the same as described above.

For example, in the above Chemical Formulae 1a to 1d, the $T^1$, $T^2$, $T^3$, $T^4$, and $T^5$ may independently be one selected from groups listed in the following Group 1.

The optoelectronic material may be, for example, represented by one of the following Chemical Formulae 2aa to 2cb, but is not limited thereto.

[Chemical Formula 2aa]
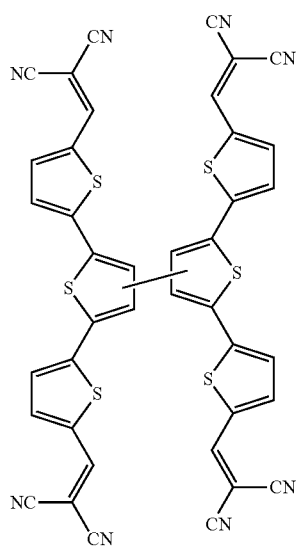
[Chemical Formula 2ba]
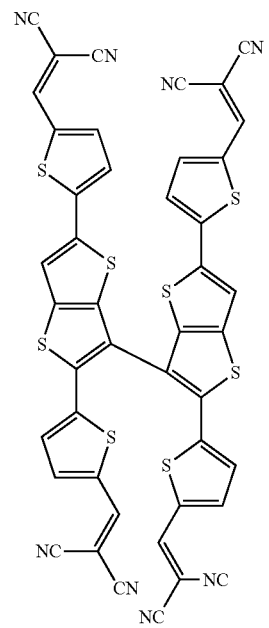
[Chemical Formula 2ab]
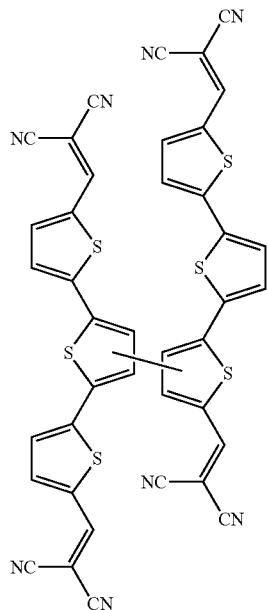
[Chemical Formula 2bb]
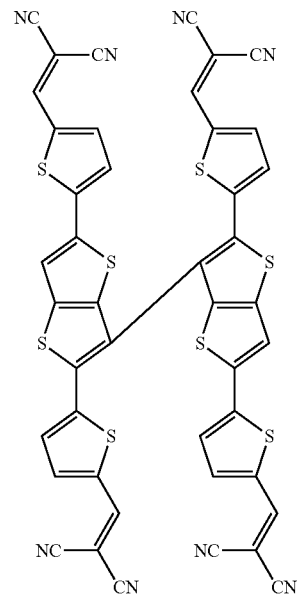

[Chemical Formula 2bc]

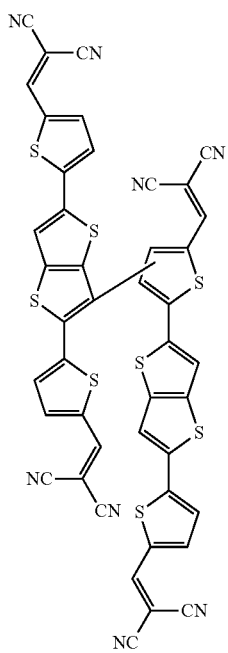

[Chemical Formula 2ca]

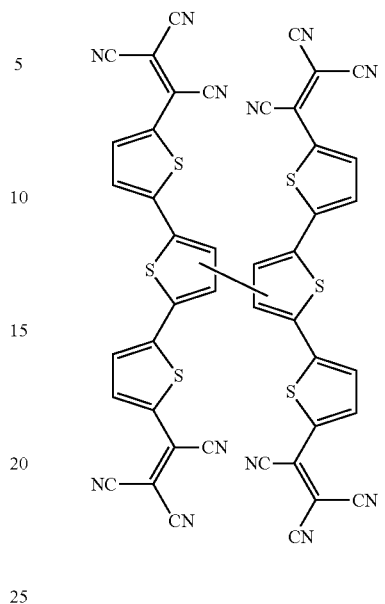

[Chemical Formula 2cb]

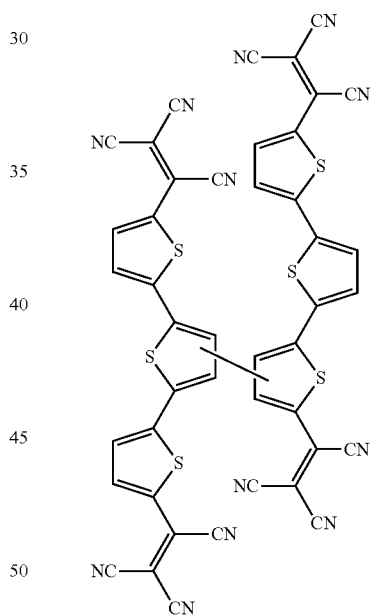

[Chemical Formula 2bd]

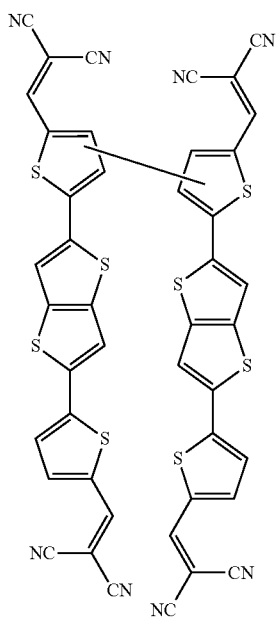

The optoelectronic material may, for example, selectively absorb light in a green wavelength region, and may have a HOMO level of about 5.0 to about 7.0 eV and an energy bandgap of about 1.9 to about 2.8 eV. When the optoelectronic material has the HOMO level and energy bandgap within the ranges, it may be applied as a semiconductor that effectively absorbs light in a green wavelength region and thus it has it has high external quantum efficiency (EQE) thereby improving photoelectric conversion efficiency.

The optoelectronic material may show an absorption curve having a relatively narrow full width at half maximum (FWHM) of about 50 nm to 150 nm in a thin film state. Herein, the FWHM is a width of a wavelength corresponding to a half of a maximum absorption point, and a smaller width at half maximum indicates selective absorption of light in a narrow wavelength region and a high wavelength. Accordingly, a compound having a FWHM within the range may have high wavelength selectivity for a green wavelength region.

Hereinafter, an organic optoelectronic device including the optoelectronic material according to example embodiments is described referring to the drawings.

FIG. 1 is a cross-sectional view showing an organic optoelectronic device according to example embodiments.

Referring to FIG. 1, an organic optoelectronic device 100 according to example embodiments includes a first electrode 10 and a second electrode 20 facing each other, and an active layer 30 interposed between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor, i.e., indium tin oxide (ITO) or indium zinc oxide (IZO), or a metal thin layer of a thin monolayer or multilayer. When one of the first electrode 10 and the second electrode 20 is a non-light-transmitting electrode, the one of the first electrode 10 and the second electrode 20 may be made of, for example, an opaque conductor such as aluminum (Al).

The active layer 30 includes a p-type semiconductor material and an n-type semiconductor material to form a pn junction, and absorbs light externally to generate excitons and then to separate the generated excitons into holes and electrons.

The active layer 30 includes the above optoelectronic material.

The above optoelectronic material may, for example, selectively absorb light in a green wavelength region, and the active layer 30 may selectively absorb light in a green wavelength having a maximum absorption wavelength ($\lambda_{max}$) at about 500 nm to about 580 nm.

The active layer 30 may show a relatively narrow absorption curve having a full width at half maximum (FWHM) of about 50 nm to about 150 nm. Accordingly, the active layer 30 may have high selectivity for light in a green wavelength region.

The optoelectronic material may be an n-type semiconductor or a p-type semiconductor in the active layer 30. When the optoelectronic material is applied as an n-type semiconductor, a p-type semiconductor may be further included with the n-type semiconductor to form a pn junction, and while when the optoelectronic material is applied as a p-type semiconductor, an n-type semiconductor may be further included with the p-type semiconductor to form a pn junction.

For example, when the optoelectronic material is an n-type semiconductor, a p-type semiconductor represented by the following Chemical Formula 3 may be further included.

[Chemical Formula 3]

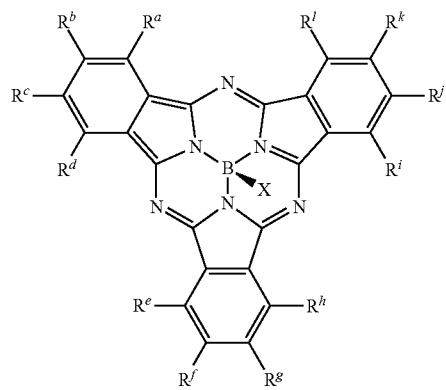

In the above Chemical Formula 3,

Each of $R^a$ to $R^l$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a halogen-containing group, and a combination thereof, and X is an anion.

The compound represented by the above Chemical Formula 3 may be, for example, at least one of compounds represented by the following Chemical Formulae 3a to 3e, but is not limited thereto.

[Chemical Formula 3a]

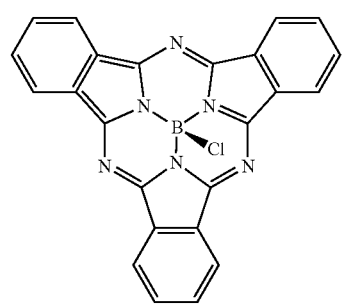

[Chemical Formula 3b]

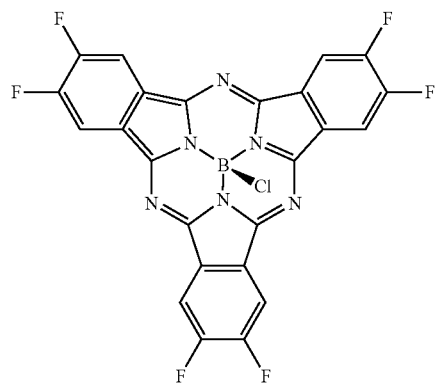

-continued

[Chemical Formula 3c]

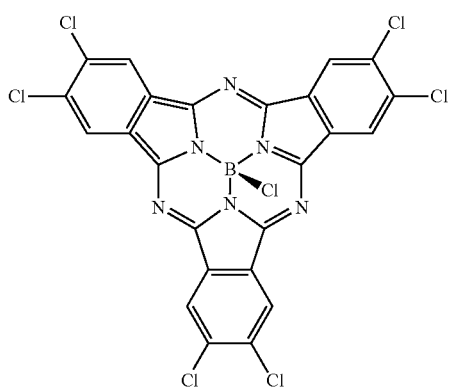

[Chemical Formula 3d]

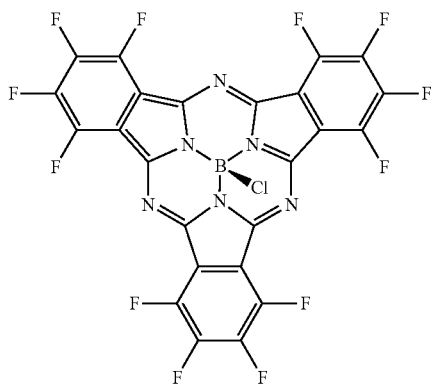

[Chemical Formula 3e]

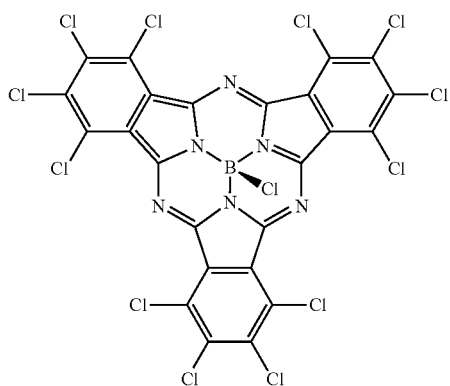

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the p-type semiconductor compound and the n-type semiconductor compound in a thickness ratio of about 1:100 to about 100:1. The compounds may be included in a thickness ratio ranging from about 1:50 to about 50:1 within the range, specifically, about 1:10 to about 10:1, and more specifically, about 1:1. When the p-type and n-type semiconductors have a composition ratio within the range, an exciton may be effectively produced and a pn junction may be effectively formed.

The p-type layer may include the p-type semiconductor compound, and the n-type layer may include the n-type semiconductor compound.

The active layer 30 may have a thickness of about 1 nm to about 500 nm, and specifically, about 5 nm to about 300 nm. When the active layer 30 has a thickness within the range, the active layer may effectively absorb light, effectively separate holes from electrons, and deliver them, thereby effectively improving photoelectric conversion efficiency.

In the organic optoelectronic device 100, when light enters from the first electrode 10 and/or second electrode 20, and when the active layer 30 absorbs light having a predetermined wavelength region, excitons may be produced from the inside. The excitons are separated into holes and electrons in the active layer 30, and the separated holes are transported to an anode that is one of the first electrode 10 and second electrode 20 and the separated electrons are transported to the cathode that is the other of and the first electrode 10 and second electrode 20 so as to flow a current in the organic optoelectronic device.

Figure 2:
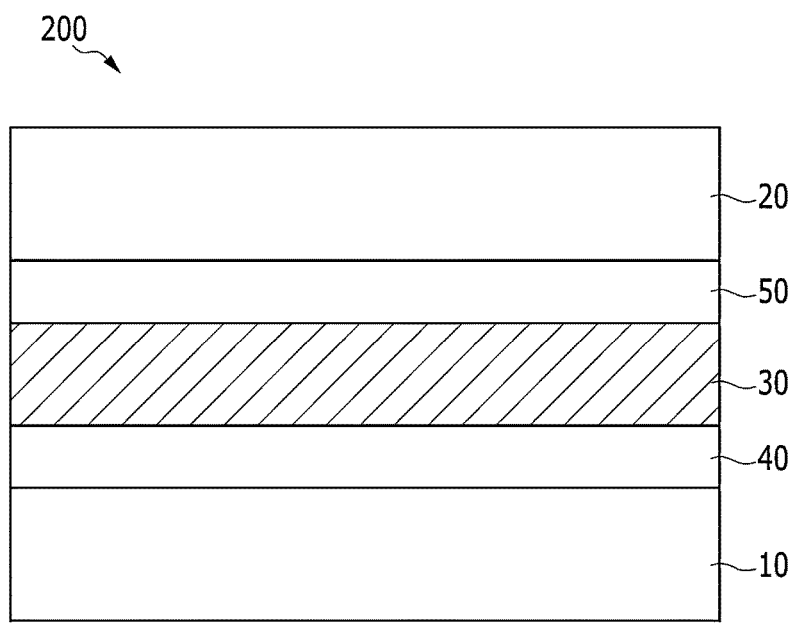
FIG. 2 is a cross-sectional view showing an organic optoelectronic device according to example embodiments.

Referring to FIG. 2, an organic optoelectronic device according to example embodiments is described.

FIG. 2 is a cross-sectional view of an organic optoelectronic device according to example embodiments.

Referring to FIG. 2, an organic optoelectronic device 200 according to example embodiments includes a first electrode 10 and a second electrode 20 facing each other, and an active layer 30 interposed between the first electrode 10 and the second electrode 20, like the example embodiment illustrated in FIG. 1.

However, the organic optoelectronic device 100 according to example embodiments further includes charge auxiliary layers 40 and 50 between the first electrode 10 and the active layer 30, and the second electrode 20 and the active layer 30, unlike the example embodiment illustrated in FIG. 1. The charge auxiliary layers 40 and 50 may facilitate the transfer of holes and electrons separated from the active layer 30, so as to increase efficiency.

The charge auxiliary layers 40 and 50 may be at least one selected from a hole injection layer (HIL) for facilitating hole injection, a hole transport layer (HTL) for facilitating hole transport, an electron blocking layer (EBL) for preventing or inhibiting electron transport, an electron injection layer (EIL) for facilitating electron injection, an electron transport layer (ETL) for facilitating electron transport, and a hole blocking layer (HBL) for preventing or inhibiting hole transport.

The charge auxiliary layers 40 and 50 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly (styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N, N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 50 may be omitted.

The organic optoelectronic device may be applied to various fields, for example a solar cell, an image sensor, a photo-detector, a photo-sensor, and an organic light emitting diode (OLED), but is not limited thereto.

Hereinafter, an example of an image sensor including the organic optoelectronic device is described referring to drawings. As an example of an image sensor, an organic CMOS image sensor is described.

Figure 3:
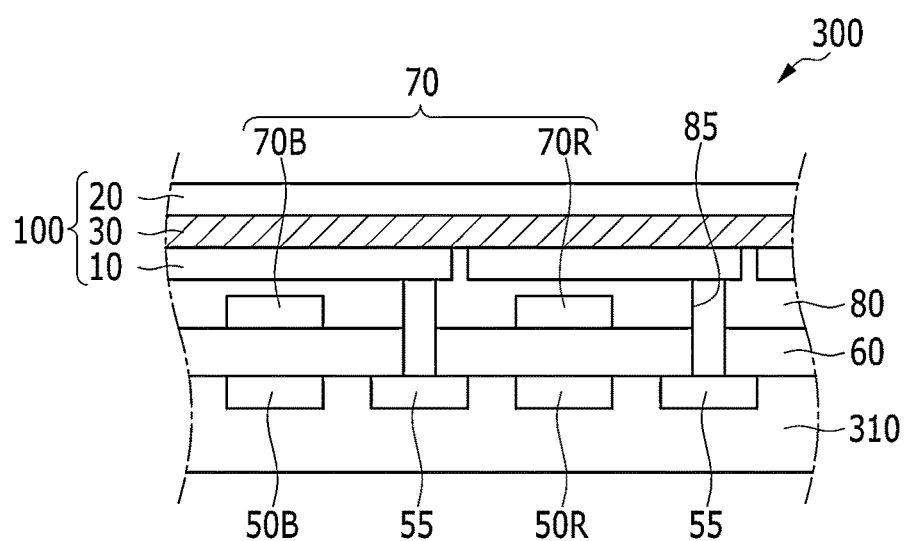
FIG. 3 is a cross-sectional view showing a CMOS image sensor according to example embodiments.

FIG. 3 is a cross-sectional view showing an organic CMOS image sensor according to example embodiments.

FIG. 3 illustrates blue, green, and red pixels that are adjacent to one another, but is not limited thereto.

Referring to FIG. 3, an organic CMOS image sensor 300 according to example embodiments includes a semiconductor substrate 310 integrated with photo-sensing devices 50B and 50R, a transmission transistor (not shown), and a charge storage device 55, a lower insulation layer 60, a color filter layer 70, an upper insulation layer 80, and an organic optoelectronic device 100.

The semiconductor substrate 310 may be a silicon substrate, and is integrated with the photo-sensing device 50, the transmission transistor (not shown), and the charge storage device 55. The photo-sensing devices 50B and 50R may be photodiodes.

The photo-sensing devices 50B and 50R, the transmission transistor, and/or the charge storage device 55 may be integrated in each pixel, and as shown in the drawing, the photo-sensing devices 50B and 50R may be included in a blue pixel and a red pixel and the charge storage device 55 may be included in a green pixel.

The photo-sensing devices 50B and 50R sense light, the information sensed by the photo-sensing devices may be transferred by the transmission transistor, and the charge storage device 55 is electrically connected with the organic optoelectronic device 100, so the information of the charge storage device 55 may be transferred by the transmission transistor.

A metal wire (not shown) and a pad (not shown) are formed on the semiconductor substrate 310. In order to decrease signal delay, the metal wire and pad may be made of a metal having relatively low resistivity, for example, aluminum (Al), copper (Cu), silver (Ag), and alloys thereof, but is not limited thereto. However, the metal wire and pad are not limited to this structure, and the metal wire and pad may be positioned under the photo-sensing devices 50B and 50R.

The lower insulation layer 60 is formed on the metal wire and the pad. The lower insulation layer 60 may be made of an inorganic insulating material, e.g., a silicon oxide and/or a silicon nitride, or a low dielectric constant (low K) material such as SiC, SiCOH, SiCO, and SiOF. The lower insulation layer 60 has a trench exposing the charge storage device 55. The trench may be filled with fillers.

A color filter layer 70 is formed on the lower insulation layer 60. The color filter layer 70 includes a blue filter 70B formed in the blue pixel and a red filter 70R filled in the red pixel. In example embodiments, a green filter is not included, but a green filter may be further included.

The upper insulation layer 80 is formed on the color filter layer 70. The upper insulation layer 80 may eliminate a step caused by the color filter layer 70 and smoothes the surface. The upper insulation layer 80 and lower insulation layer 60 may include a contact hole (not shown) exposing a pad, and a through-hole 85 exposing the charge storage 55 of a green pixel.

The organic optoelectronic device 100 is formed on the upper insulation layer 80. The organic optoelectronic device 100 includes the first electrode 10, the active layer 30, and the second electrode 120 as described above.

The first electrode 10 and the second electrode 20 may be transparent electrodes, and the active layer 30 selectively absorbs light in a green wavelength region as described above and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in a photo-sensing device 50B and 50R.

Figure 4:
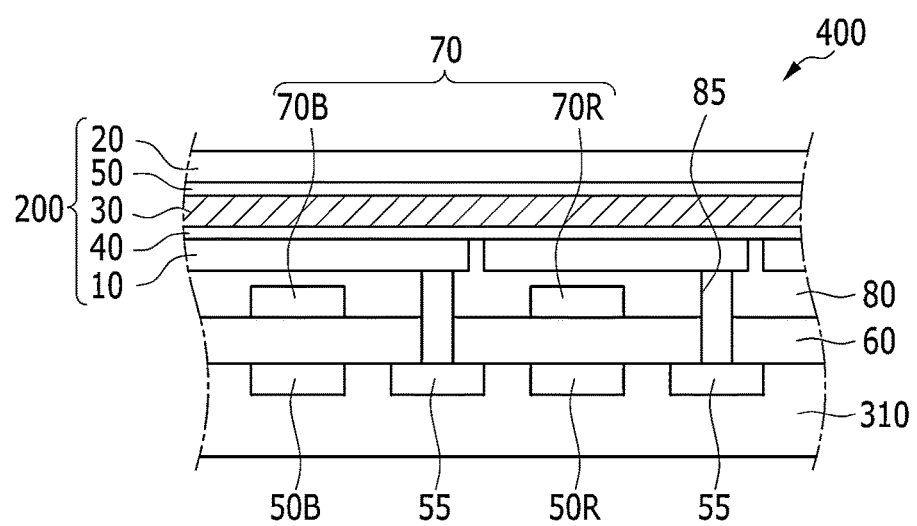
FIG. 4 is a cross-sectional view showing a CMOS image sensor according to example embodiments.

FIG. 4 is cross-sectional view showing an organic CMOS image sensor according to example embodiments.

Referring to FIG. 4, an organic CMOS image sensor 300 according to example embodiments includes a semiconductor substrate 310 integrated with photo-sensing devices 50B and 50R, a transmission transistor (not shown), and a charge storage device 55, a lower insulation layer 60, a color filter layer 70, an upper insulation layer 80, and an organic optoelectronic device 100, like the example embodiment illustrated in FIG. 3.

However, the organic optoelectronic device 100 further includes charge auxiliary layers 40 and 50. The charge auxiliary layers 40 and 50 are the same as described above, and one of the charge auxiliary layers 40 and 50 may be omitted.

Hereinafter, the present disclosure is illustrated in more detail with reference to examples. However, these are examples, and the present disclosure is not limited thereto.

SYNTHESIS OF OPTOELECTRONIC MATERIAL

Comparative Synthesis Example 1

2,2':5',2"-terthiophene (Sigma-Aldrich Co. LLC. (99%)) represented by the following Chemical Formula A is prepared.

[Chemical Formula A]

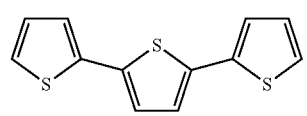

Comparative Synthesis Example 2

Synthesis of 5,5"-formyl-2,2':5',2'-terthiophene 1.50 g (4.2 mmol) of terthiophene and 50 mL of tetrahydrofuran (THF) as a solvent are put in a glass reactor under an N₂ atmosphere, and 6.25 mL of n-BuLi (a 1.6 M solution in n-hexane, 10.0 mmol) is subsequently added thereto at a low temperature (−78° C.). Then, the mixture is agitated for 2 hours, 0.84 mL (10.8 mmol) of dimethylformamide (DMF) is added thereto, acetic acid is used to complete the reaction, and CH₂Cl₂ is used to perform extraction, obtaining 5,5"-formyl-2,2':5',2"-terthiophene.

Synthesis of 5,5"-bis(dicyanovinyl)-2,2":5',2"-terthiophene 1.50 g (3.6 mmol) of the obtained 5,5"-formyl-2,2':5',2'-terthiophene, 0.52 g (7.9 mmol) of malononitrile, and 8 mg (0.1 mmol) of b-alanine are sequentially put in a reactor, 100 mL of ethanol is added thereto, and the mixture is agitated and heated (refluxed) for 2 hours. After removing a solvent in the reactor, THF is added thereto, and the reactant is purified through a silica gel column, obtaining 5,5"-bis(dicyanovinyl)-2,2':5',2"-terthiophene.

Synthesis Example 1

[Reaction Scheme 1]

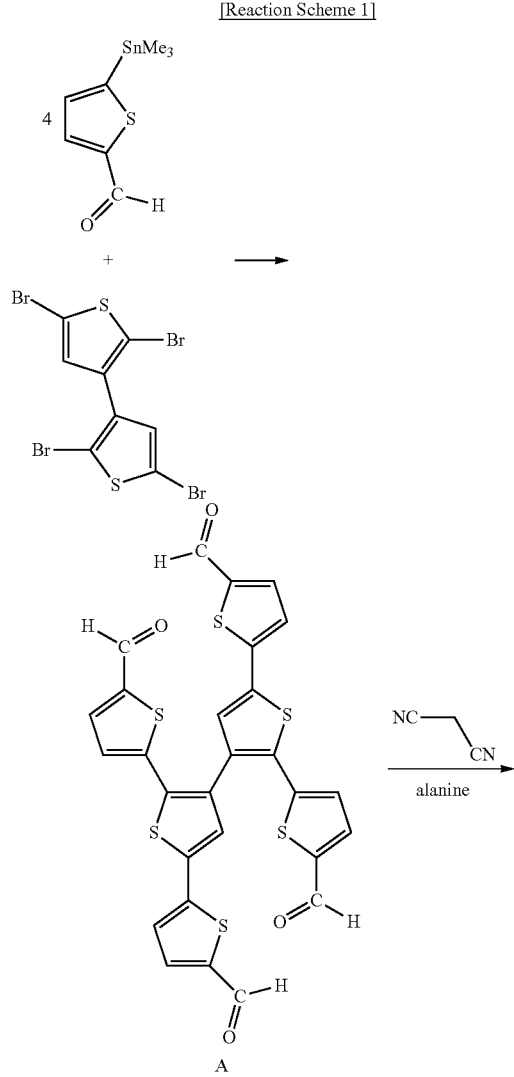

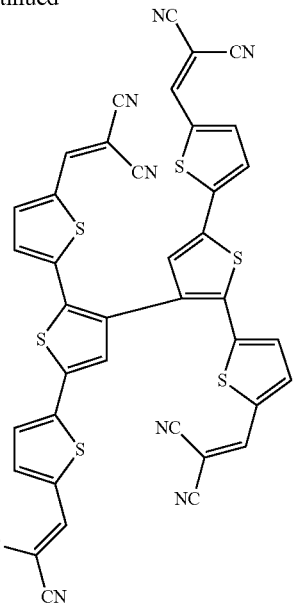

[Chemical Formula 2aa-1]

0.48 g (0.001 mol) of 2,2',5,5'-tetrabromo-3,3'-bithiophene (C₈H₂Br₄S₂, a molecular weight of 481.8475 g/mole) (Sigma-Aldrich Co. LLC.) and 1.098 g (0.004 mol) of (trimethylstannyl)thiophene-2-carbaldehyde (MW: 274.95 g/mole) are added to 20 ml of DMF/toluene (dimethylformamide/toluene, a volume ratio=1/4), 23 mg of Pd(PPh₃)₄ as a catalyst is additionally added thereto, and the mixture is agitated. After heating and reacting the resultant, acetic acid is used to complete the reaction, and CH₂Cl₂ is used to perform extraction, obtaining a compound A. Subsequently, a compound represented by Chemical Formula 2aa-1 is obtained through the same process as Comparative Synthesis Example 2.

Subsequently, the obtained compound, malononitrile, and b-alanine are sequentially put in a reactor according to the same method as Comparative Synthesis Example 2, 100 mL of ethanol is added thereto, and the mixture is agitated and heated (refluxed) for 2 hours. After removing a solvent in the reactor, THF is added thereto, and the reactant is purified through a silica gel column, obtaining a compound represented by Chemical Formula 2aa-1.

Evaluation I
Evaluation 1

The design structure of the compounds according to Synthesis Example 1 and Comparative Synthesis Examples 1 and 2 and the actual structure of the compound according to Synthesis Example 1 are examined.

The actual structure of the compound according to Synthesis Example 1 is examined with NMR (500 MHz, Bruker Corp.).

Figure 5:
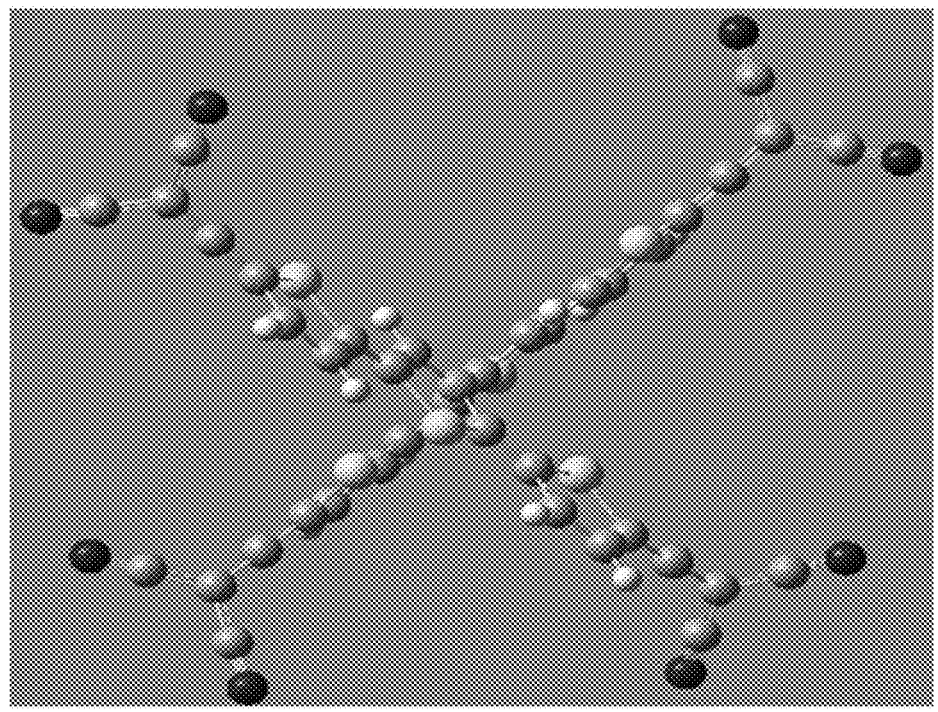
FIG. 5 shows the design structure of the compound according to Synthesis Example 1.
Figure 6:
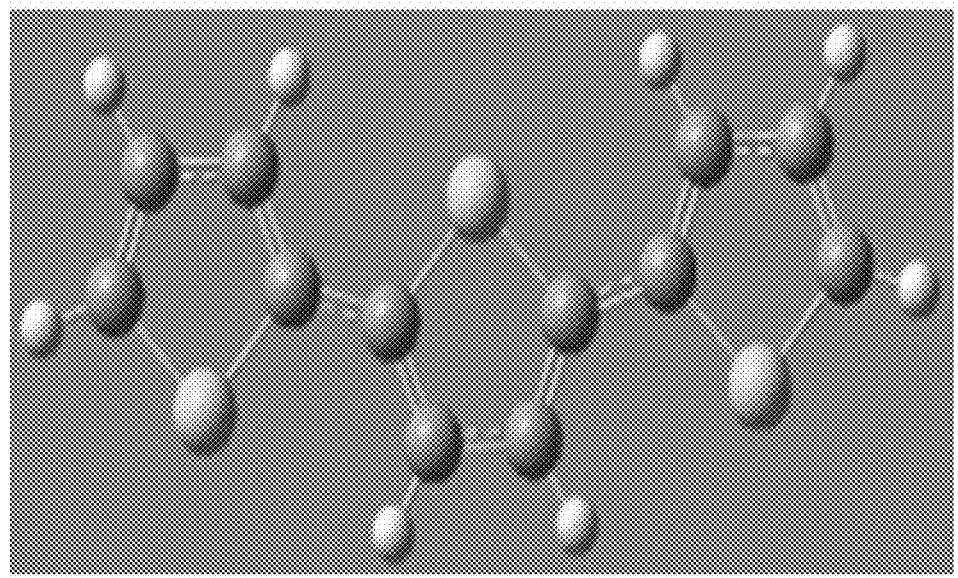
FIG. 6 shows the design structure of the compound according to Comparative Synthesis Example 1.
Figure 7:
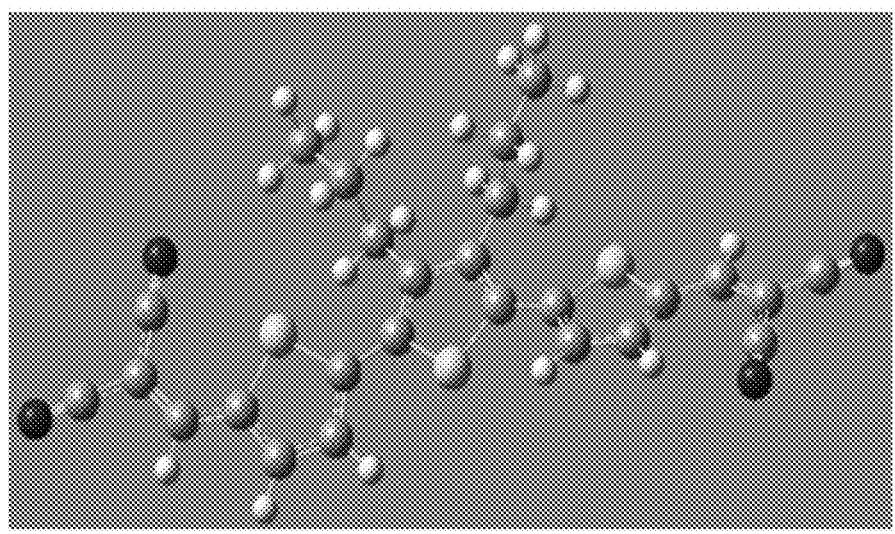
FIG. 7 shows the design structure of the compound according to Comparative Synthesis Example 2.

FIG. 5 shows the design structure of the compound according to Synthesis Example 1, FIG. 6 shows the design structure of the compound according to Comparative Synthesis Example 1, and FIG. 7 shows the design structure of the compound according to Comparative Synthesis Example 2.

Figure 8:
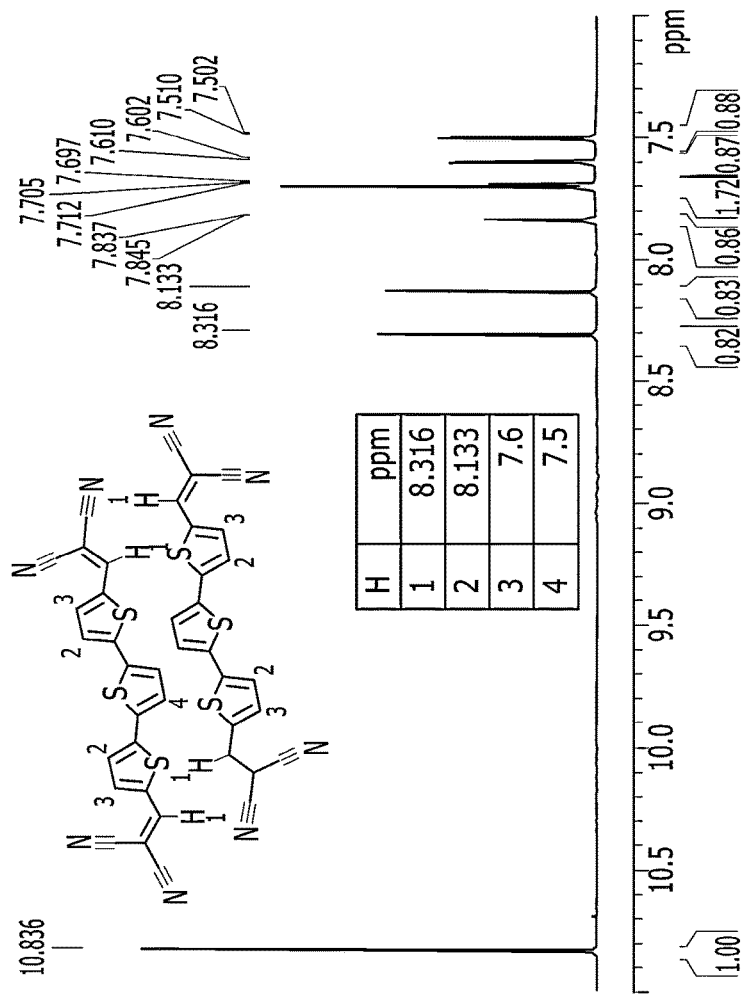
FIG. 8 shows NMR data of the compound according to Synthesis Example 1.

FIG. 8 shows NMR data of the compound according to Synthesis Example 1.

As shown in FIG. 5, the compound is designed to have a structure in which two terthiophene derivatives are crosslinked, and the structure is different from the structure of the compounds according to Comparative Synthesis Examples 1 and 2 as shown in FIGS. 6 and 7. In addition, as shown in FIG. 8, a compound represented by the above Chemical Formula 2aa-1 is found to be actually obtained.

Evaluation 2

Light absorption characteristics of the compounds according to Synthesis Example 1 and Comparative Synthesis Examples 1 and 2 are evaluated.

Figure 9:
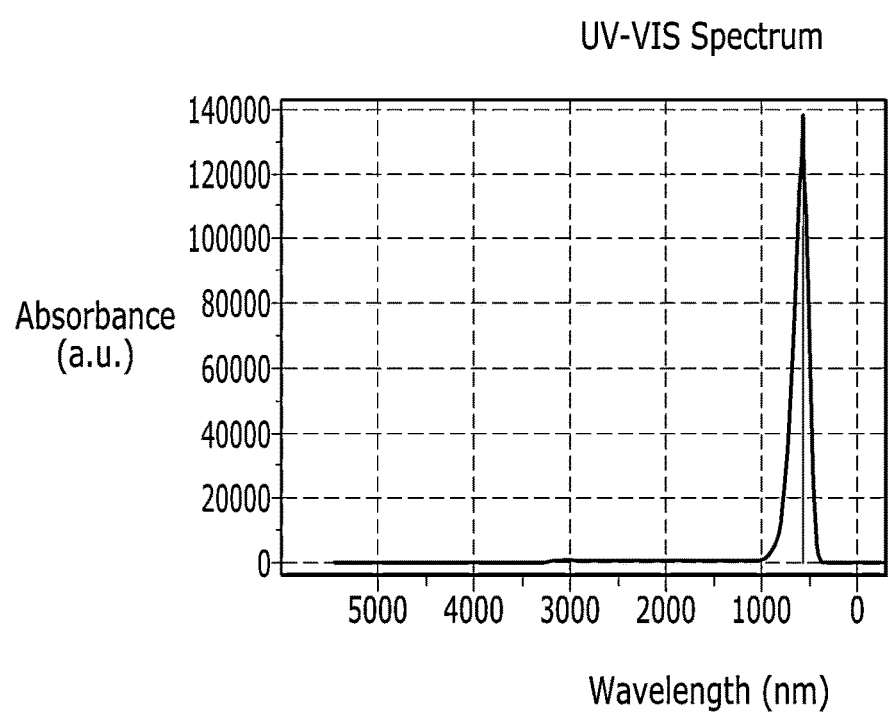
FIG. 9 is a graph showing light absorption characteristics of the compound according to Synthesis Example 1.
Figure 10:
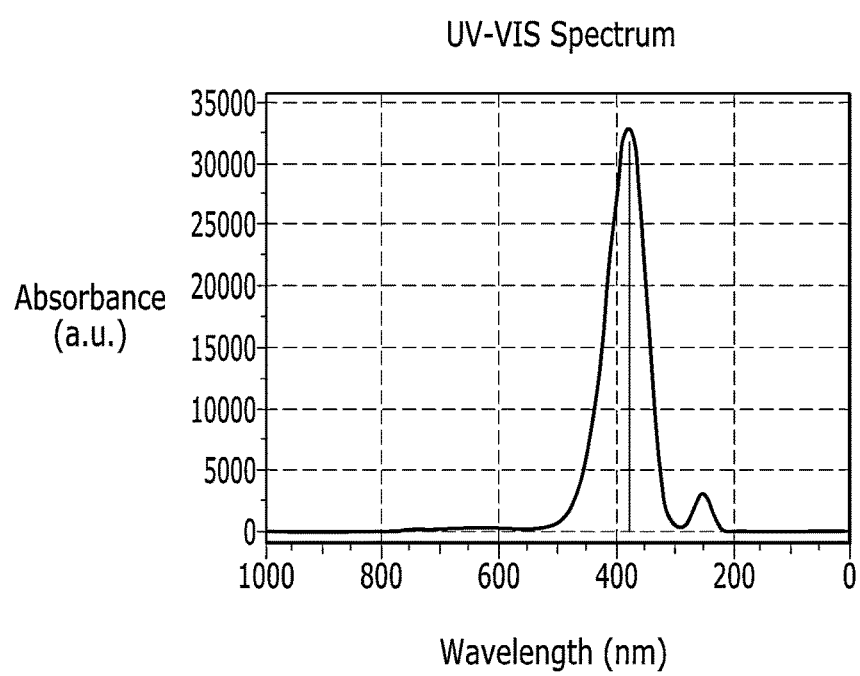
FIG. 10 is a graph showing light absorption characteristics of the compound according to Comparative Synthesis Example 1.
Figure 11:
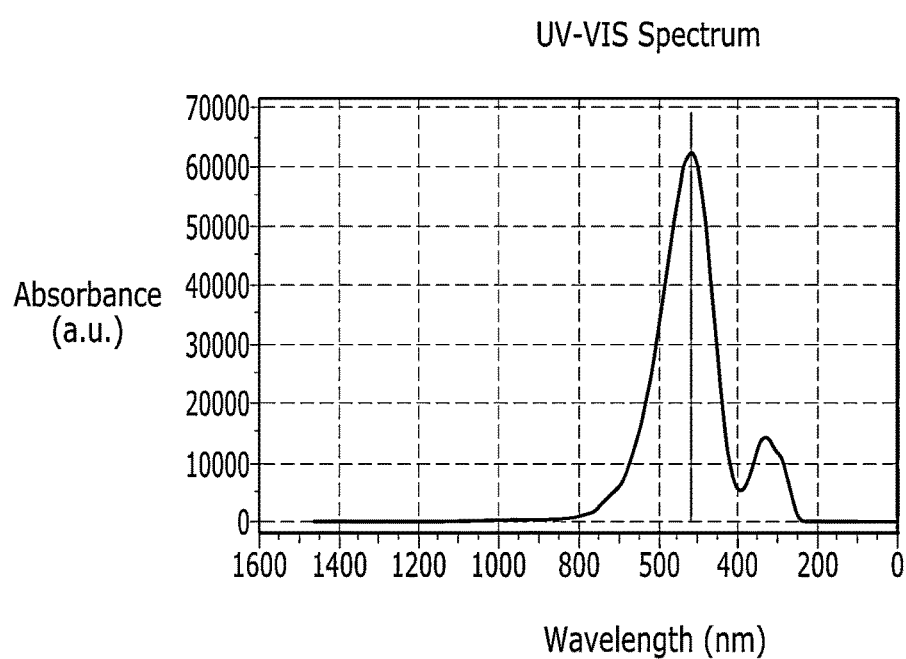
FIG. 11 is a graph showing light absorption characteristics of the compound according to Comparative Synthesis Example 2.

FIG. 9 is a graph showing light absorption characteristics of the compound according to Synthesis Example 1, FIG. 10 is a graph showing light absorption characteristics of the compound according to Comparative Synthesis Example 1, and FIG. 11 is a graph showing light absorption characteristics of the compound according to Comparative Synthesis Example 2.

The absorbance of the compounds is calculated based on FIGS. 9 to 11, and the results are provided in Table 1.

TABLE 1

|  | Absorbance (calculation value) |
| --- | --- |
| Synthesis Example 1 | about 120,000 |
| Comparative Synthesis Example 1 | about 30,000 |
| Comparative Synthesis Example 2 | about 60,000 |

Referring to FIGS. 9 to 11 and Table 1, the compound according to Synthesis Example 1 shows improved absorption characteristics compared with the compound according to Comparative Synthesis Example 1.

Evaluation 3

Light absorption characteristics of the compounds according to Synthesis Example 1 and Comparative Synthesis Example 2 in a thin film state are evaluated.

The light absorption characteristics in a thin film state are evaluated by thermally depositing each compound according to Synthesis Example 1 and Comparative Synthesis Example 2 under high vacuum (<$10^{-7}$ Torr) at a speed of 0.5 to 1.0 Å/s to respectively form a 50 nm to 100 nm-thick thin film, and then radiating ultraviolet-visible rays (UV-Vis) with a Cary 5000 UV spectroscope (Varian Medical Systems, Inc.).

Figure 12:
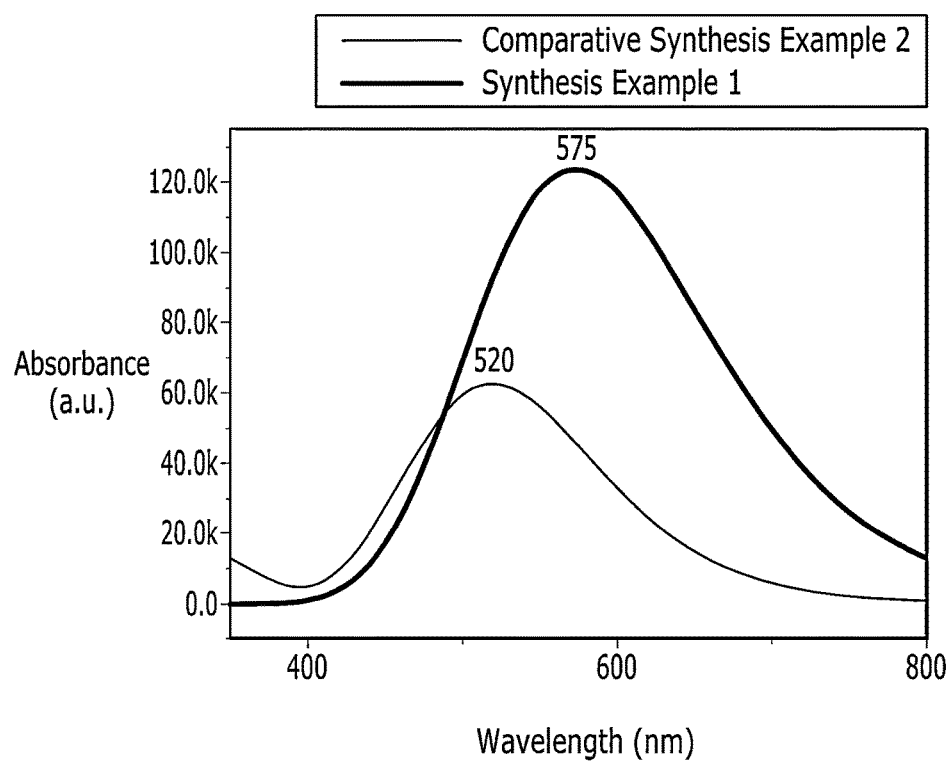
FIG. 12 is a graph showing light absorption characteristics of thin films respectively including the compounds according to Synthesis Example 1 and Comparative Synthesis Example 2 depending on a wavelength.

The results are provided in FIG. 12.

FIG. 12 is a graph showing light absorption characteristics of the thin films respectively including the compounds according to Synthesis Example 1 and Comparative Synthesis Example 2 depending on a wavelength.

Referring to FIG. 12, the compounds according to Synthesis Example 1 and Comparative Synthesis Example 2 have a maximum light absorption wavelength ($\lambda_{max}$) in a range of about 500 nm to 600 nm, but the compound according to Synthesis Example 1 is found to have a higher extinction coefficient and a narrower full width at half maximum than those of the compound according to Comparative Synthesis Example 2. Accordingly, the compound according to Synthesis Example 1 shows improved light absorption characteristics and wavelength selectivity compared with the compound according to Comparative Synthesis Example 2.

Evaluation 4

Thermal stability of the compound according to Synthesis Example 1 is evaluated.

The thermal stability is evaluated in a thermogravimetric analysis (TGA) method using Discovery TGA (TA Instruments) and a differential scanning calorimetry (DSC) method using Discovery DSC (TA Instruments)

Figure 13:
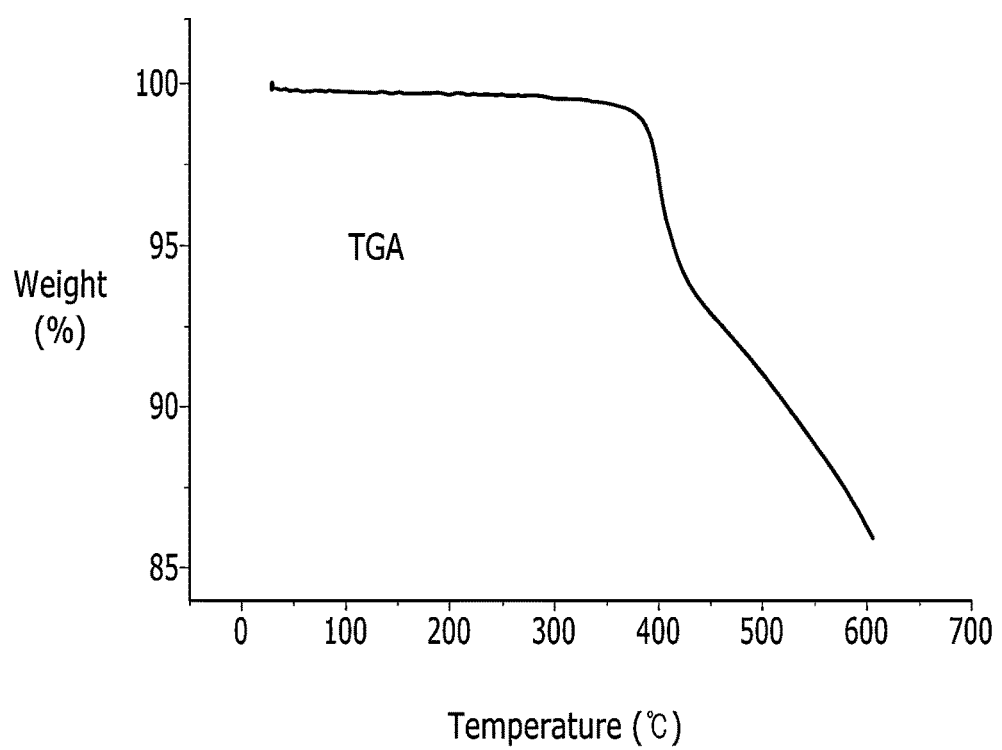
FIG. 13 is a graph showing thermogravimetric analysis results of the compound according to Synthesis Example 1.
Figure 14:
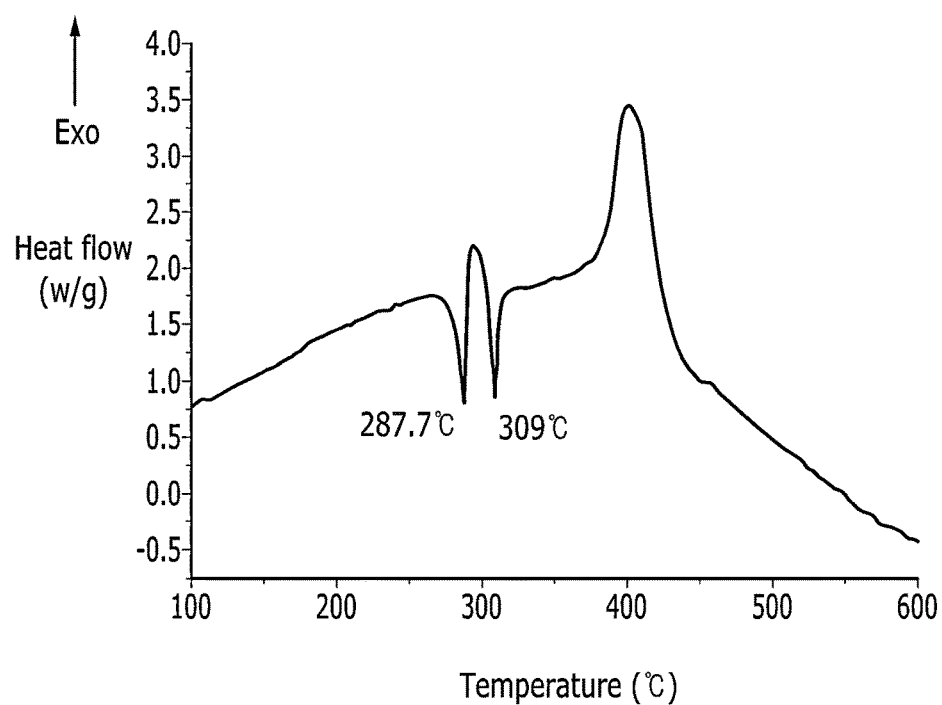
FIG. 14 is a graph showing differential scanning calorimetry results of the compound according to Synthesis Example 1.

FIG. 13 is a graph showing the thermogravimetric analysis result of the compound according to Synthesis Example 1, and FIG. 14 is a graph showing the differential scanning calorimetry result of the compound according to Synthesis Example 1.

Referring to FIGS. 13 and 14, the compound according to Synthesis Example 1 is found to maintain thermal stability up to about 350 to 400° C., and thus is expected to secure thermal stability at a process temperature ranging from about 120 to 200° C.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. An optoelectronic material comprising a first organic molecule and a second organic molecule that are independently represented by the following Chemical Formula 1:

[Chemical Formula 1]

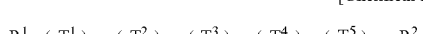

wherein, in Chemical Formula 1,
$T^1$, $T^2$, $T^3$, $T^4$, and $T^5$ are independently a substituted or unsubstituted thiophene moiety,
n1 to n5 are independently 0 or 1,
at least one of n1 to n5 is 1, and
$R^1$ is represented by the following Chemical Formula A and $R^2$ is represented by the following Chemical Formula B, respectively,

[Chemical Formula A]

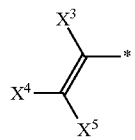

[Chemical Formula B]

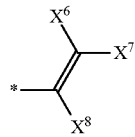

wherein, in Chemical Formulae A and B,
$X^3$ to $X^8$ are independently hydrogen, a substituted or unsubstituted $C_1$-$C_{30}$ alkyl group, a substituted or unsubstituted $C_6$-$C_{30}$ aryl group, a substituted or unsubstituted $C_3$-$C_{30}$ heteroaryl group, a substituted or unsubstituted $C_1$-$C_{30}$ alkoxy group, a cyano group, or a combination thereof, and
wherein one of $T^1$, $T^2$, $T^3$, $T^4$, and $T^5$ of the first organic molecule are linked with one of $T^1$, $T^2$, $T^3$, $T^4$, and $T^5$ of the second organic molecule.

2. The optoelectronic material of claim 1, wherein the optoelectronic material is represented by one of the following Chemical Formulae 1a to 1m:

[Chemical Formula 1a]

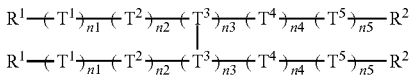

[Chemical Formula 1b]

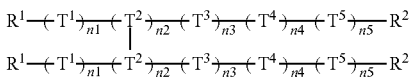

[Chemical Formula 1c]

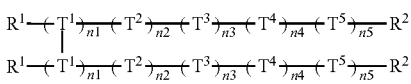

[Chemical Formula 1d]

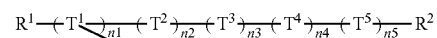

[Chemical Formula 1e]

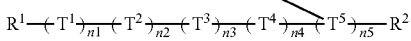

[Chemical Formula 1f]

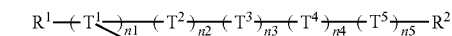

[Chemical Formula 1g]

[Chemical Formula 1h]

[Chemical Formula 1i]

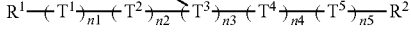

[Chemical Formula 1j]

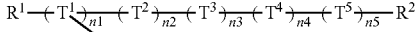

[Chemical Formula 1k]

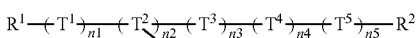

[Chemical Formula 1l]

-continued

[Chemical Formula 1m]

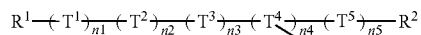

wherein, in the above Chemical Formulae 1a to 1m, $R^1$, $R^2$, $T^1$, $T^2$, $T^3$, $T^4$, $T^5$, n1 to n5 are defined as in claim 1.

3. The optoelectronic material of claim 1, wherein the $T^1$, $T^2$, $T^3$, $T^4$, and $T^5$ are independently selected from groups listed in the following Group 1:

[Group 1]

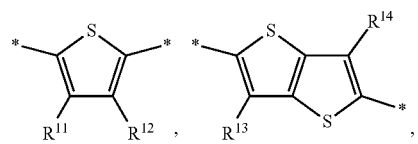

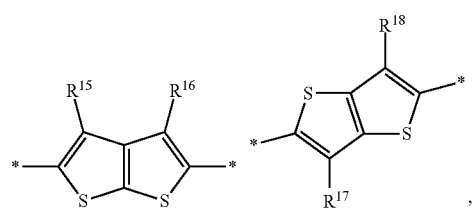

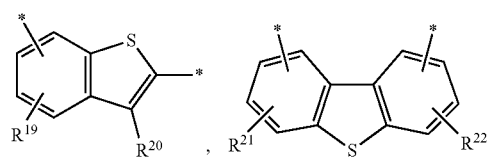

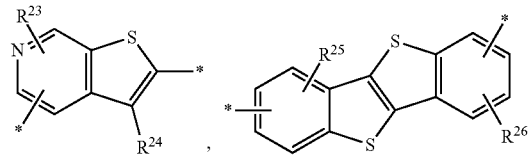

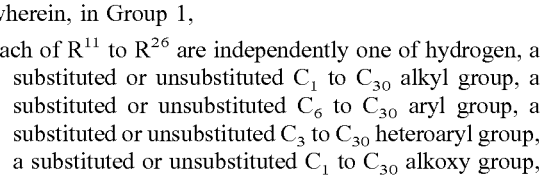

wherein, in Group 1, each of $R^{11}$ to $R^{26}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, and a combination thereof, or a point linked with the first organic molecule or the second organic molecule.

4. The optoelectronic material of claim 3, wherein the one of $R^{11}$ to $R^{26}$ of $T^1$, $T^2$, $T^3$, $T^4$, and $T^5$ of the first organic molecule is linked with one of $R^{11}$ to $R^{26}$ of $T^1$, $T^2$, $T^3$, $T^4$, and $T^5$ of the second organic molecule.

5. The optoelectronic material of claim 1, wherein the first organic molecule and the second organic molecule are independently represented by the following Chemical Formula 2:

[Chemical Formula 2]

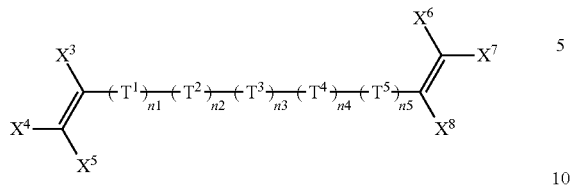

wherein, in Chemical Formula 2, each of $T^1$, $T^2$, $T^3$, $T^4$, $T^5$, and n1 to n5 are defined as in claim 1, and $X^3$ to $X^8$ are independently hydrogen, a substituted or unsubstituted $C_1$-$C_{30}$ alkyl group, a substituted or unsubstituted $C_6$-$C_{30}$ aryl group, a substituted or unsubstituted $C_3$-$C_{30}$ heteroaryl group, a substituted or unsubstituted $C_1$-$C_{30}$ alkoxy group, a cyano group, or a combination thereof, provided that at least one of $X^3$ to $X^8$ is a cyano group.

6. The optoelectronic material of claim 1, wherein the first organic molecule and the second organic molecule are independently represented by one of the following Chemical Formulae 2a to 2c:

[Chemical Formula 2a]

[Chemical Formula 2a]

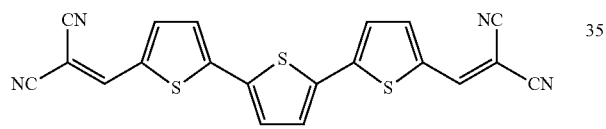

[Chemical Formula 2b]

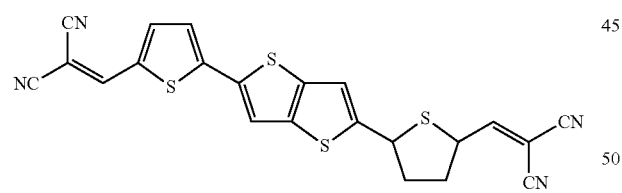

[Chemical Formula 2c]

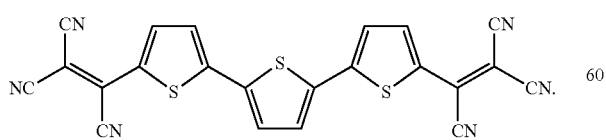

7. The optoelectronic material of claim 6, wherein the optoelectronic material is represented by one of the following Chemical Formulae 2aa to 2cb:

[Chemical Formula 2aa]

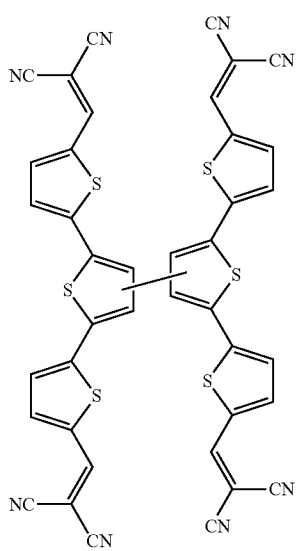

[Chemical Formula 2ab]

[Chemical Formula 2ba]
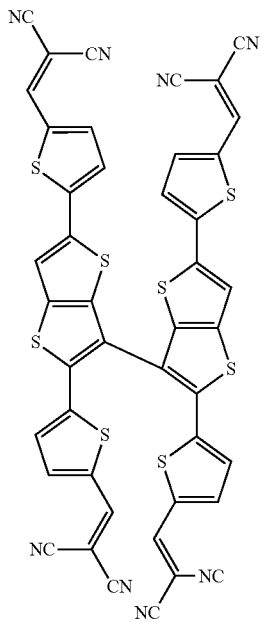
[Chemical Formula 2bb]
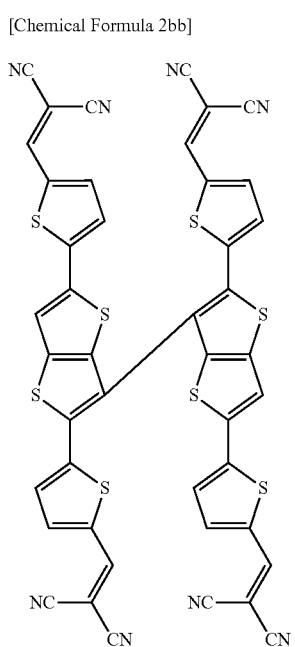
[Chemical Formula 2bc]
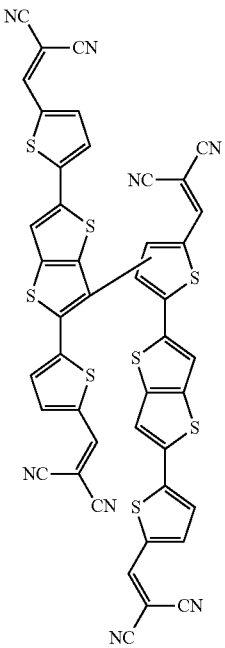
[Chemical Formula 2bd]
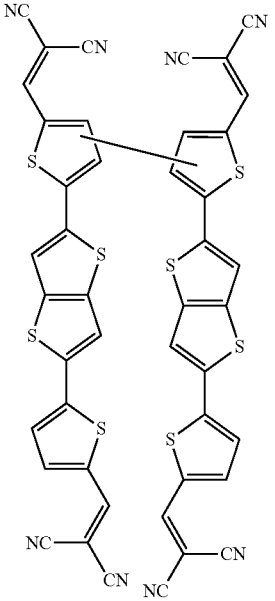

-continued

[Chemical Formula 2ca]

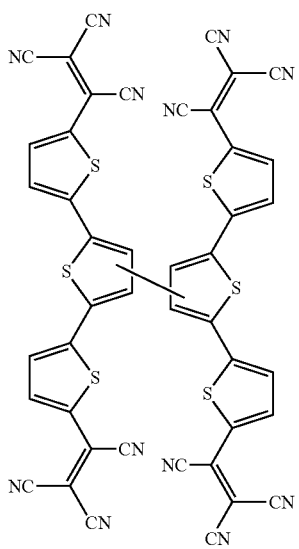

[Chemical Formula 2cb]

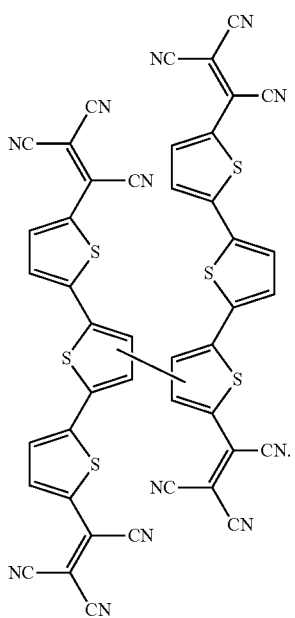

8. The optoelectronic material of claim 1, wherein the first organic molecule and the second organic molecule absorb light in one of a blue wavelength region, a red wavelength region, and a green wavelength region.

9. The optoelectronic material of claim 8, wherein
the blue wavelength region has a maximum absorption wavelength ($\lambda_{max}$) at greater than or equal to about 400 nm and less than about 500 nm,
the red wavelength region has a maximum absorption wavelength ($\lambda_{max}$) at greater than about 580 nm and less than or equal to about 700 nm, and
the green wavelength region has a maximum absorption wavelength ($\lambda_{max}$) at about 500 nm to about 580 nm.

10. The optoelectronic material of claim 1, wherein the first organic molecule and the second organic molecule are the same compound.

11. The optoelectronic material of claim 1, wherein the optoelectronic material has a bandgap of about 1.9 to about 2.8 eV.

12. An organic optoelectronic device comprising:
an anode and a cathode facing each other; and
an active layer between the anode and the cathode, the active layer including the optoelectronic material of claim 1.

13. The organic optoelectronic device of claim 12, wherein the organic optoelectronic device selectively absorbs light in a green wavelength region.

14. The organic optoelectronic device of claim 12, wherein the active layer further comprises a compound represented by the following Chemical Formula 3:

[Chemical Formula 3]

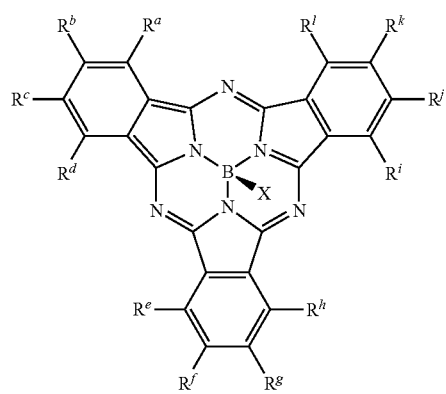

wherein, in the above Chemical Formula 3,
each of $R^a$ to $R^l$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a halogen, a halogen-containing group, and a combination thereof, and
X is an anion.

15. The organic optoelectronic device of claim 14, wherein the compound represented by the above Chemical Formula 3comprises at least one of compounds represented by the following Chemical Formulae 3a to 3e:

[Chemical Formula 3a]

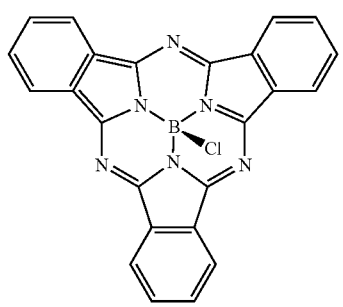

-continued

[Chemical Formula 3b]

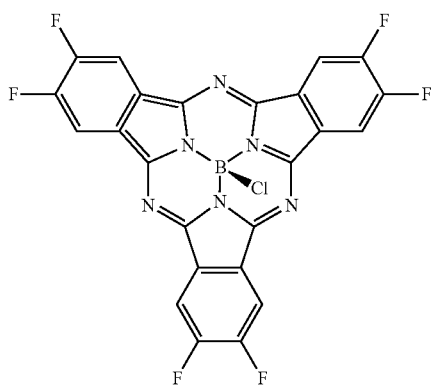

[Chemical Formula 3c]

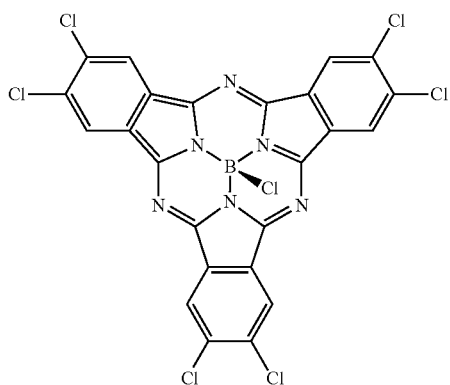

[Chemical Formula 3d]

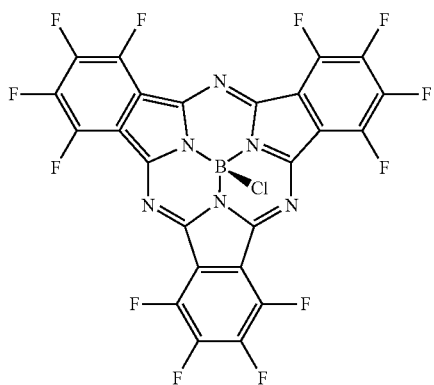

-continued

[Chemical Formula 3e]

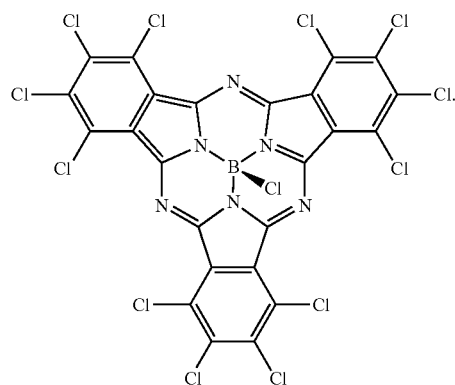

16. An image sensor comprising the organic optoelectronic device of claim 12.

17. The image sensor of claim 16, wherein the image sensor comprises:

a semiconductor substrate integrated with a plurality of a first photo-sensing devices sensing light in a blue wavelength region and a plurality of a second photo-sensing device sensing light in a red wavelength region;

a color filter layer on the semiconductor substrate, the color filter layer including a blue filter that selectively absorbs light in a blue wavelength region and a red filter that selectively absorbs light in a red wavelength region; and the organic optoelectronic device on the color filter layer.

18. The image sensor of claim 16, wherein the organic optoelectronic device selectively absorbs light in a green wavelength region.

* * * * *